(12) United States Patent
Matsumae et al.

(10) Patent No.: US 6,440,155 B1
(45) Date of Patent: Aug. 27, 2002

(54) DEVICE FOR HEATING A BIOTISSUE EMPLOYING A STRONG LIGHT

(75) Inventors: Mitsunori Matsumae, Isehara (JP); Michihiro Kaneda, Tokyo (JP)

(73) Assignees: Tokai University Educational System, Tokyo (JP); Nippon Infrared Industries Co., Ltd., Tokyo (JP)

( * ) Notice: Subject to any disclaimer, the term of this patent is extended or adjusted under 35 U.S.C. 154(b) by 0 days.

(21) Appl. No.: 09/374,866

(22) Filed: Aug. 16, 1999

(30) Foreign Application Priority Data

Aug. 19, 1998  (JP) .......................................... 10-249134

(51) Int. Cl.[7] .............................................. A61N 5/006
(52) U.S. Cl. .............................. 607/88; 607/91; 607/96; 606/10; 606/11; 606/12; 606/31; 604/20; 604/113
(58) Field of Search ........................ 607/88–92; 604/20, 604/113; 128/303.1; 606/10–12, 31

(56) References Cited

U.S. PATENT DOCUMENTS

| | | | | |
|---|---|---|---|---|
| 4,614,190 A | * | 9/1986 | Stanco et al. ............... 128/395 |
| 5,222,953 A | * | 6/1993 | Dowlatshahi ................ 606/15 |
| 5,298,026 A | | 3/1994 | Chang | |
| 5,643,334 A | * | 7/1997 | Eckhouse et al. ............. 607/88 |
| 5,657,760 A | | 8/1997 | Ying et al. | |
| 5,662,643 A | | 9/1997 | Kung et al. | |
| 5,707,401 A | * | 1/1998 | Talmore ....................... 607/88 |
| 5,720,772 A | * | 2/1998 | Eckhouse ..................... 607/88 |
| 5,814,008 A | * | 9/1998 | Chen et al. ................... 604/21 |
| 5,814,078 A | * | 9/1998 | Zhou et al. ..................... 607/1 |
| 5,830,209 A | * | 11/1998 | Savage et al. ................ 606/15 |
| 5,849,026 A | * | 12/1998 | Zhou et al. ................... 607/90 |
| 5,957,960 A | * | 9/1999 | Chen et al. ................... 607/92 |

FOREIGN PATENT DOCUMENTS

WO      WO 92/10142      6/1992

* cited by examiner

Primary Examiner—Linda C. M. Dvorak
Assistant Examiner—A. Farah
(74) Attorney, Agent, or Firm—Flynn, Thiel, Boutell & Tanis, P.C.

(57) ABSTRACT

A device for heating a biotissue employing a strong light, characterized in that, in thermotherapy comprising leading a biotissue to necrosis by heating the biotissue by a strong light from a light source, in order to lead a predetermined biotissue to necrosis in a temperature region before reaching tissue transpiration during the raising of the temperature of said biotissue, temperature measurement is performed by a temperature meter measuring the spatial temperature distribution of the biotissue at real time, and that the light output of the light source, the on-time of intermittent irradiation and the off-time of intermittent irradiation are controlled on the basis of the information at real time to accomplish remedial conditions.

8 Claims, 3 Drawing Sheets

TARGET TEMPERATURE DISTRIBUTION

DEVICE FOR HEATING A BIOTISSUE EMPLOYING A STRONG LIGHT

BACKGROUND OF THE INVENTION

1. Field of the Invention

The present invention relates to a device for heating a biotissue employing a strong light, and more specifically, a relates to a device for heating a biotissue employing a strong light which performs a treatment by a strong light, a such as laser light, for example, by destroying a predetermined biotissue in the brain.

2. Prior Art

Laser light has been applied like a surgical knife to remove tumors and other cancers in the medical field. As thermotherapy can be mentioned a treatment comprising the heating of a biotissue of a tumor and the like, leading the tissue to necrosis in a temperature region before reaching tissue transpiration during the raising of the temperature of the biotissue, and removing the biotissue in the target region.

In thermotherapy, in particular, in the case of once starting transpiration in heating by light, light transmission to a farther inner part is inhibited by a carbonized tissue with a very high absorbance in the neighborhood of an irradiation point, and a rapid temperature rise occurs locally. In the case of performing thermotherapy, such a phenomenon following the transpiration becomes a problem in the following points (1)–(2); for example, if there occurs such an inhibition and transpiration following a temperature rise in the removal of a tumor in the brain, it can have an influence upon a normal tissue around the tumor and cause a fatal functional disorder.

(1) In the case of irradiation in a tissue, a gas generated as a result of transpiration has a high pressure and a high temperature (100° C. or more), and oppression may occur to a peripheral tissue by pressure, and thermal influence upon the peripheral tissue by the high-temperature gas, and thermal influence upon the circumference of a flow path in the case of the high-temperature gas exiting.

(2) Since the inner face of the transpiration part is covered with a carbonized tissue, light transmission to a farther inner part is inhibited, and fails to perform heating in a wide range.

SUMMARY OF THE INVENTION

Hence, it is the object of the present invention to provide a device for heating a biotissue employing strong light, characterized in that, in thermotherapy comprising accomplishing thermal denaturation by heating a biotissue by the irradiation of a strong light employing a light source, such as laser light, a spatial temperature distribution in vivo is measured at real time, and that the light source is controlled on the basis of the spatial and time-related information to form. a desired temperature distribution at a predetermined and desired region in the biotissue.

The present invention provides a device for heating a biotissue employing strong light, characterized in that, in thermotherapy comprising leading a biotissue to necrosis by heating the biotissue by strong light from a light source, in order to lead a predetermined biotissue to necrosis in a temperature region before reaching tissue transpiration during the raising of the temperature of said biotissue, a temperature measurement is performed by a temperature meter measuring the spatial temperature distribution of the biotissue at real time, and the light output of the light source, the on-time of intermittent irradiation and the off-time of intermittent irradiation are controlled on the basis of the information at real time to accomplish remedial conditions.

In addition, the present invention provides a heating apparatus employing a strong light to be used for the thermal remedy of a biotissue comprising (a) a temperature-measuring device measuring a biotissue requiring treatment and a spatial temperature distribution at its peripheral region at real time, (b) a controlling device controlling the light output of a light source, the time of intermittent irradiation on and the time of intermittent irradiation off at real time by comparing predetermined remedial conditions with a temperature value measured by said temperature-measuring device, (c) a light source emitting a strong light by being controlled by said controlling device, and (d) an optical fiber which is inserted into a living body and introduces said strong light into the biotissue requiring treatment, which is characterized in that the temperature of the biotissue is raised by said strong light and the biotissue requiring treatment is necrotized in a temperature region before resulting in tissue transpiration.

PREFERRED EMBODIMENTS

In thermotherapy, a predetermined biotissue is allowed to face the tip of an optical fiber, and a strong light is irradiated from the tip to lead the predetermined biotissue to necrosis. In the present invention, the upper limit and the lower limit of a heating temperature of the biotissue is strictly controlled according to the above constitution in thermotherapy. They are determined by the conditions of the upper limit temperature (Th), namely, a temperature causing no tissue transpiration, and the lower limit temperature (Tl), namely, a biotissue necrosis temperature. As a strong light, any strong light capable of leading a biotissue to necrosis by heating the biotissue can be employed, but laser light is preferably employed.

In the present invention, a target region for thermotherapy is a biotissue in vivo to be removed as a prerequisite of treatment. The biotissue includes a denatured tissue of a normal one and different kinds of tissues, and the present invention can be applied to any of them. As examples can be mentioned the destruction of a tumor tissue, a remedy for a pain caused by a cancer, and the destruction of a specific central nervous tissue as a remedy for various symptoms of Parkinson's disease.

Hereunder, while the case of employing laser light as one example with a tumor tissue will be described, it is also true of other biotissues and the case of employing a strong light other than laser light. In thermotherapy, it is necessary to keep normal tissue from being damaged to necrotize only tumor tissue. Though the necrosis temperature varies according to the kind of a biotissue, it is about 42° C. in the case of a tumor. The tumor has a complicated form, and in the case that there exists a delicate tissue (tissue having an important function, for example, in the brain) at a position near the tumor, it is important to decide a region while taking safety into consideration.

Figure 1:
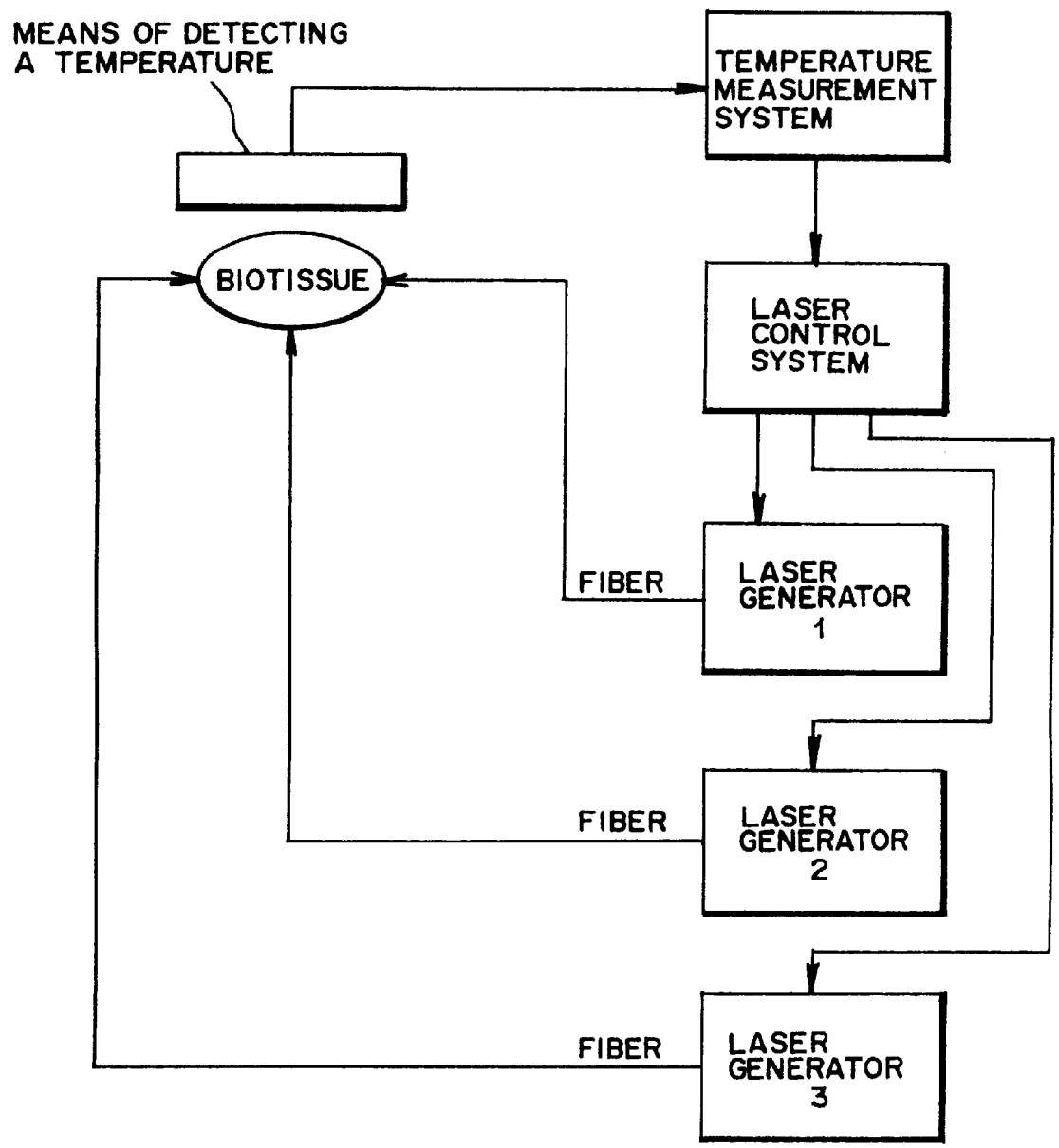
FIG. 1 is a schematic view showing the gist of the present invention.

FIG. 1 is a schematic view showing the gist of the present invention. In FIG. 1,as laser generators are shown three laser generators 1-3, but the laser generator may be employed singly, or a plurality of laser generators may be employed on demand. The number thereof is selected properly according to the size of a biotissue. Laser light is irradiated onto a biotissue from the generator through an optical fiber from the tip thereof. The generation and termination of the laser light are performed in accordance with measured temperature values, as will be described later.

In FIG. 1, temperature values of a predetermined biotissue of a tumor and the like and the circumference thereof are detected by a means for detecting a temperature (a temperature meter). As the temperature meter can be employed any means capable of detecting a three-dimensional temperature distribution like MRI, at real time. The measured temperature values obtained are transferred to a laser control system from a temperature measurement system. There, the output of a laser generator is controlled on the basis of the measured temperature values. In the laser control system, the laser output is modulated to a pattern programed in advance on the basis of the information upon the obtained temperature distribution, and thereby a feedback control is performed at, real time.

In the present invention, it is a prerequisite to lead a predetermined biotissue to necrosis in a temperature region before reaching tissue transpiration during the raising of the temperature of the biotissue. For a tumor, it necrotizes at about 42° C. In the case of irradiating a strong light like laser light thereon, it is extremely important to prevent the tissue from vaporizing and transpiring and not to destroy normal tissue around it.

If the biotissue vaporizes and transpires, the gas generated has a high pressure and a high temperature (100° C. or more), and there occurs oppression to a peripheral tissue by pressure, thermal influence upon the peripheral tissue by the high-temperature gas, and thermal influence upon the circumference of a flow path in the case of the high-temperature gas exiting, which can cause a fatal functional disorder upon normal tissue around the tumor. Moreover, since the inner face of the transpiration part is covered with a carbonated tissue, a farther inner light tansmission is inhibited to fail to heat a necessary site.

Figure 2:
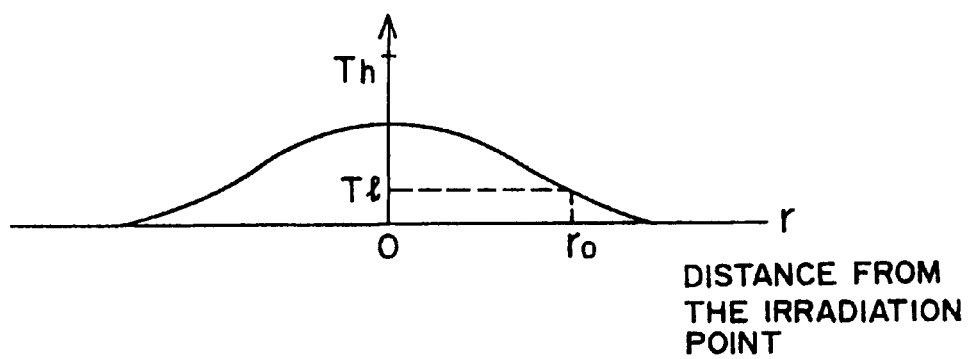
FIG. 2 is a diagram showing "a temperature distributions is a target biotissue" in the present invention.

FIG. 2 is a. diagram showing "a temperature distribution in a target biotissue" of an important prerequisite in the present invention. 0 in FIG. 2 shows a laser light irradiation point. T shows the temperature of the irradiation point, Tl a necrosis temperature, and Th a temperature at which a destroyed component evaporates. It is necessary to strictly control the temperature lest it be beyond the temperature Th in irradiation. r shows the distance from the irradiation point. ro shows the end part of the tumor, and the following part is a part of a normal tissue. The part from the irradiation point 0 to the end part ro of the tumor is necrotized by heating by irradiation, but the part of a normal tissue should not be necrotized.

It is important, from this viewpoint, to perform the control of the laser generator output based on the measured temperature values so that the temperature distrubution T of the tumor (target region for thermotherapy=biotissue in vivo to be removed on a prerequisite of a remedy) should become Tl<T<Th, with Tl as the lower limit temperature and Th as the upper limit temperature. It is very difficult, however, to obtain such a temperature distribution as in FIG. 2 according to ordinary irradiation.

Hence, in the present invention, temperature measurement is performed by a temperature meter measuring the spatial temperature distribution of the biotissue as in FIG. 2 at real time, and the light output P of the light source, the on-time of intermittent irradiation and the off-time of intermittent irradiation are controlled on the basis of the information at real time to accomplish remedial conditions. As control elements therefor, namely, control parameters, are employed the number of points and arrangement of. laser irradiation, the wavelength ($\lambda$) of the irradiated laser light, the ouput the laser light, the on-time of intermittent irradiation and the off-time of intermittent irradiation.

Figure 3:
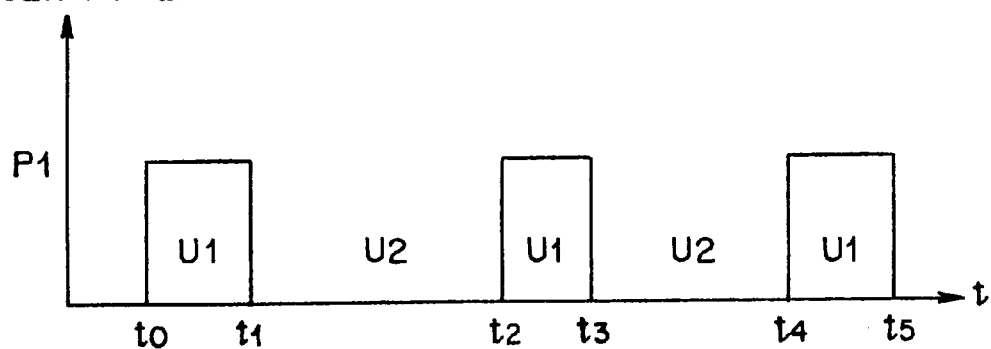
FIG. 3 is a chart showing the operation of the present invention.

FIGS. 3–4 are diagrams showing embodiments of the operation under the above remedial conditions. In FIGS. 3–4, the irradiation on-time is shown as U1 and the irradiation off-time as U2. FIG. 4(e) shows a target temperature distribution in a biotissue of a tumor and the like. Laser light is irradiated by the output P1 of laser light at the point of to. Then, as shown in FIG. 4(a), the biotemperature rises locally with the irradiation point at the center. At this time, the irradiation termination point t1 is controlled so as not to reach the upper limit temperature Th. For this control, it is advantageous to employ a light source with a variable wavelength in addition to irradiation time.

In the above control, as shown in FIG. 1, the temperature distribution is detected by a temperature measurement system including a means for detecting a temperature, and controlled by a laser control system on the basis thereof. In addition, the laser light irradiation, for example, to a cerebral tumor, is performed by opening a small hole in a skull, allowing an optical fiber to pass through it, and allowing the tip thereof to face a site to be irradiated. The arrangement of the position of the tip can be performed by operating, for example, on the basis of an X-ray image.

Figure 4A:
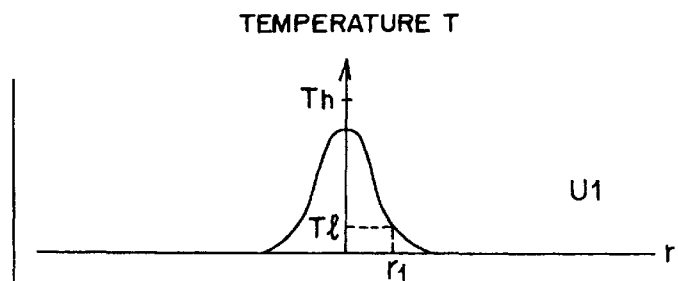
FIG. 4 is another chart showing the operation of the present invention.
Figure 4B:
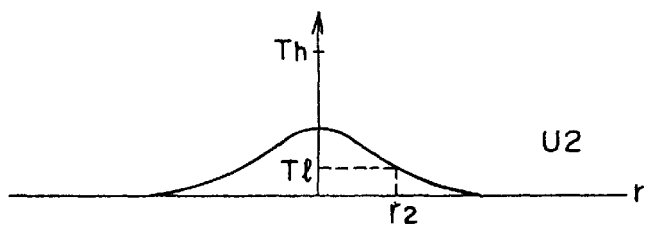
Figure 4C:
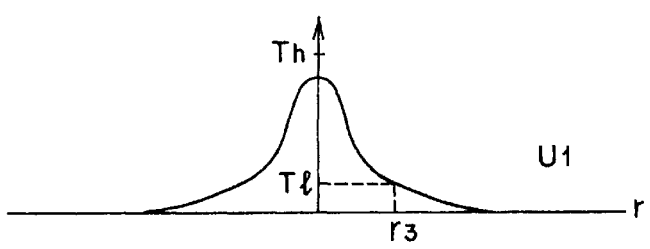

After the irradiation termination point t1, the heat of a locally high-temperature part is transmitted to the neighborhood, and the temperature distribution as shown in FIG. 4(b) is obtained with t2 time. The temperature distribution must be made so as to reach a target temperature distribution of FIG. 4(e), but the end part ro of the tumor cannot be necrotized yet in the state of FIG. 4(b). Hence, irradiation is performed again. At this time the irradiation termination point t3 is controlled so as not to reach the upper limit temperature Th. FIG. 4(c) shows this state.

Figure 4E:
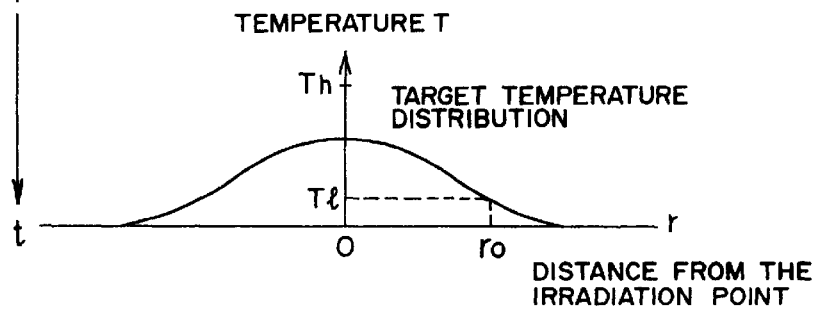

The above operation is repeated necessary times to obtain the temperature distribution of FIG. 4(e), namely, FIG. 2, finally. Thereby, the tumor can be necrotized without necrotizing normal tissue.

Besides, since the irradiation is controlled to a temperature before reaching tissue transpiration at this time, the destruction thereof can be performed without any influence upon normal tissue, and the formation of a carbonated tissue can be avoided. That is, since there exists no vaporization/transpiration of the tumor tissue, there occurs neither oppression to a peripheral tissue by gas pressure, nor thermal influence upon the peripheral tissue by the high-temperature gas, nor thermal influence upon the circumference of a flow path in the case of the high-temperature gas exiting, and hence, there occurs no fatal functional disorder upon normal tissue around the tumor. The necrotized biotissue is discharged outside the body from the circulatory system.

According to the present invention, in thermotherapy comprising heating a biotissue by the irradiation of a strong light employing a light source, such as laser light, to accomplish thermal denaturation, a target temperature distribution can be formed at a predetermined target region in the biotissue by measuring a spatial temperature distribution in vivo at real time and controlling the light source on the basis of the spatial and time-related information.

Thereby, the biotissue in vivo to be removed as a prerequisite of treatment, for example, a tumor alone, can be necrotized effectively and removed without any bad influence upon normal tissue and without necrotizing any normal biotissue.

EXAMPLES

Hereunder, the present invention will be described in more detail according to examples, and it goes without saying that the present invention is not restricted to the examples. As a bioheating apparatus was employed a bioheating apparatus (manufactured by Nippon Infrared Indusrtries Co., Ltd.) equipped with a device with a temperature-measuring system having a means for detecting temperature, a device with a laser controlling system and a device with a laser oscillator as shown in FIG. 1.

Example 1

A treatment for a primary brain tumor was performed employing the present bioheating apparatus. An opening was made in cranial bones near the brain tumor of a remedial target employing a medical perforator, and then a laser fiber was inserted into the opening to initiate laser light irradiation. At the same time, the temperature measurement of a region (concerned region) sufficiently covering the periphery of the targeted tumor was conducted by means of a temperature-measuring device equipped with a means for detecting temperature, and temperature changes with time obtained by the temperature measurement were transferred to the laser oscillator to perform temperature control at the part.

At this time, the treatment was conducted by heating only the brain tumor tissue to 42° C. by laser light, changing the laser output to from 1 to 10 W in order to control the temperature rise of peripheral tissue to 40° C. or less, simultaneously changing the irradiation time of laser light to from 15 to 1200 seconds, and establishing an intermittent time with no laser light irradiation performed at an optional time. The intermittent time with no laser light irradiation performed was extended according to the results of the temperature measurement of the periphery of the above targeted tumor till a peripheral normal tissue was sufficiently cooled when a temperature rise approaching 40° C. appeared on the normal tissue.

Thus, only the brain tumor tissue was necrotized without necrotizing the normal tissue at the periphery of the tumor and without having any influence upon the normal tissue.

Example 2

A treatment for a metastatic brain tumor was performed employing the method of the present invention in the same manner as in Example 1. As a result, only the brain tumor tissue was necrotized without necrotizing normal tissue at the periphery of the tumor and without having any influence upon the normal tissue.

These examples of Example 1 and Example 2 can be applied to treatment for a stereotaxic thalamotomy for Parkinson's disease, a stereotaxic thalamotomy for ballism and a tremor, a stereotaxic cingulumotomy for intractable pain and a hypothalamotomy for intractable pain.

What is claimed is:

1. A device for heating a biotissue with light comprising means for generating the light, means for irradiating the generated light on the biotissue, means for measuring the spatial temperature distribution of a region containing th biotissue areal time, means for determining whether the measured spatial temperature distribution is within a range defined by the necrosis temperature of the biotissue and the transpiration temperature of the biotissue and means for interrupting and restarting the irradiation of the generated light on the biotissue at real time based on the measured spatial temperature distribution.

2. A device for heating a biotissue as stated in claim 1, wherein the light is laser light.

3. A device for heating a biotissue as stated in claim 1, wherein the mean s for generating the light additionally comprises means for varying the wavelength of the light.

4. A device for heating a biotissue as stated in claim 1, additionally comprising a plurality of means for generating the light and a plurality of means for irradiating the generated light.

5. A heating apparatus for the thermal treatment of a biotissue with light comprising means for generating the light, an optical fiber for irradiating the generated light on the biotissue, means for measuring the spatial temperature distribution of a region containing the biotissue at real time, means for comparing the measured spatial temperature distribution with predetermined temperatures contained in a temperature range defined by the necrosis temperature of the biotissue and the transpiration temperature of the biotissue and means for interrupting and restarting the irradiation of the light on the biotissue at real time based on the comparison of the measured spatial temperature distribution with the predetermined temperatures.

6. A heating apparatus as stated in claim 5, wherein the light is laser light.

7. A heating apparatus as stated in claim 5, wherein the means for generating the light additionally comprises means for varying the wavelength of the light.

8. A heating apparatus as stated in claim 5, additionally comprising a plurality of means for generating the light and a plurality of means for irradiating the generated light.

* * * * *